(12) United States Patent
Helfinstine et al.

(10) Patent No.: US 6,754,533 B1
(45) Date of Patent: Jun. 22, 2004

(54) IMPLANTABLE MEDICAL DEVICE CONFIGURED FOR DIAGNOSTIC EMULATION

(75) Inventors: Alan R. Helfinstine, Brooklyn Center, MN (US); Steve Jensen, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 441 days.

(21) Appl. No.: 09/596,173

(22) Filed: Jun. 16, 2000

(51) Int. Cl.[7] .................................................. A61N 1/37
(52) U.S. Cl. ........................................................ 607/27
(58) Field of Search .............................. 607/9, 16, 27, 607/30, 32, 57, 60, 31, 59

(56) References Cited

U.S. PATENT DOCUMENTS

| | | | |
|---|---|---|---|
| 4,532,930 A | * | 8/1985 | Crosby et al. ................. 607/57 |
| 5,464,435 A | * | 11/1995 | Neumann ....................... 607/9 |

OTHER PUBLICATIONS

Motorola HC11 Technical Data MC68HC11F1.

* cited by examiner

Primary Examiner—George R. Evanisko
(74) Attorney, Agent, or Firm—Fredrikson & Byron, P.A.

(57) ABSTRACT

An implantable medical device with internal processor is configured for diagnostic emulation with an external processor to enhance diagnostic testing with capabilities such as faster testing and more realistic testing. The implantable medical device can be a wide variety of implantable devices such as neuro stimulators, pacemakers, defibrillators, drug delivery pumps, diagnostic recorders, cochlear implants, and the like. The external processor is coupleable to the medical device to execute software involving medical device components with a bus switch coupled to the address bus, the data bus, and the internal processor. The bus switch has a bus switch external connector that when activated is configured to couple an external processor through the address bus external connection to the address bus and the external processor through the data bus external connector to the data bus. When the external processor is coupled to the medical device, the internal processor is decoupled from the address bus and data bus.

30 Claims, 8 Drawing Sheets

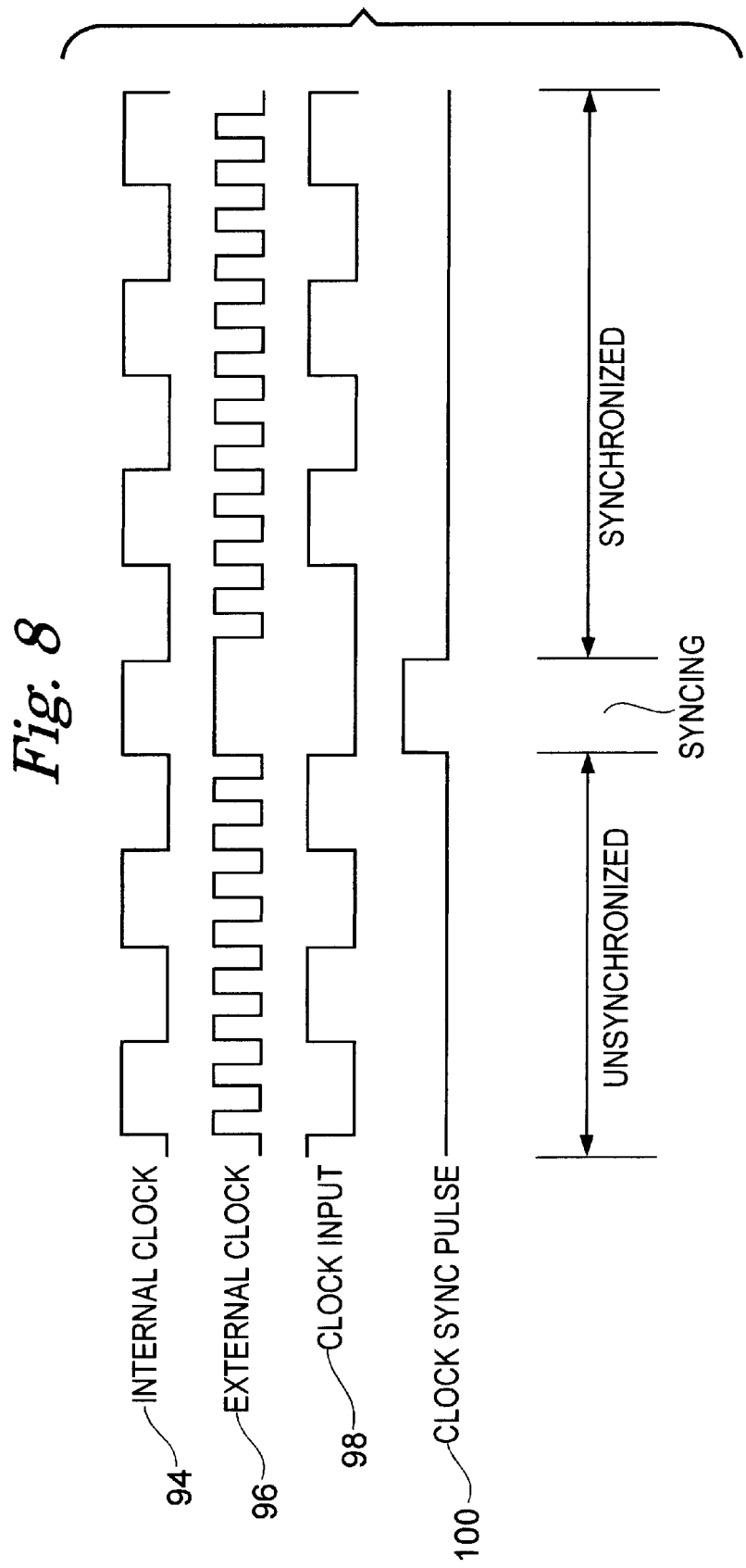

IMPLANTABLE MEDICAL DEVICE
// CONFIGURED FOR DIAGNOSTIC
// EMULATION

BACKGROUND OF THE INVENTION

This disclosure relates to a medical device and more specifically to an implantable medical device having an internal processor that executes software.

The medical device industry produces a wide variety of electronic and mechanical devices for treating patient medical conditions. Depending upon medical condition, medical devices can be surgically implanted or connected externally to the patient receiving treatment. Clinicians use medical devices alone or in combination with drug therapies and surgery to treat patient medical conditions. For some medical conditions, medical devices provide the best, and sometimes the only, therapy to restore an individual to a more healthful condition and a fuller life. Many implantable medical devices have an internal processor that executes software.

Implantable medical devices with an internal processor typically include neuro stimulators, pacemakers, defibrillators, drug delivery pumps, and diagnostic recorders. The processor executes software to perform functions that can include telemetry, power management, physiological sensing, data recording, therapy delivery, and therapy measurement. As implantable medical devices have increased in sophistication, the software executed by the internal processor has also increased in complexity, and the task of debugging the software has increased in complexity. The internal processor meets these demands while operating under a variety of constraints such as power, size, memory, speed, and the like that limit the processor's ability to perform functions other than those required for normal medical device operation. When the internal processor is tasked to perform functions not required for normal medical device operation such as developmental testing, production conformance testing, diagnostics testing, the internal processor can require a significant amount of time to perform these functions. Previous efforts to perform testing included constructing a laboratory model of the implantable medical device using different components to reduce constraints such as power, size, memory, and speed. Although a laboratory module can simulate testing, there are still differences between performance of the laboratory model and performance of the implantable medical device. The time requirements for the internal processor to perform testing can delay production and require compromises to desirable testing protocols. The results for these constraints can be increased costs, increased production time, discrepancies between laboratory product tests and production product tests, and decreased discretionary testing.

For the foregoing reasons there is a need for an implantable medical device to be configured to perform medical device functions with an internal processor and perform testing and diagnostics in another fashion.

SUMMARY OF THE INVENTION

An implantable medical device with internal processor is configured for diagnostic emulation with an external processor to enhance diagnostic testing by capabilities such as faster testing and more realistic testing. The external processor is coupleable to the medical device to execute software involving medical device components with a bus switch coupled to the address bus, the data bus, and the internal processor. The bus switch has a bus switch external connector that when activated is configured to couple an external processor through the address bus external connection to the address bus and couple the external processor through the data bus external connector to the data bus. When the external processor is coupled to the medical device, the internal processor is decoupled from the address bus and data bus.

BRIEF DESCRIPTION OF THE DRAWINGS

FIG. 8 shows a clock synchronization timing diagram embodiment.

DETAILED DESCRIPTION OF THE PREFERRED EMBODIMENTS

Figure 1A:
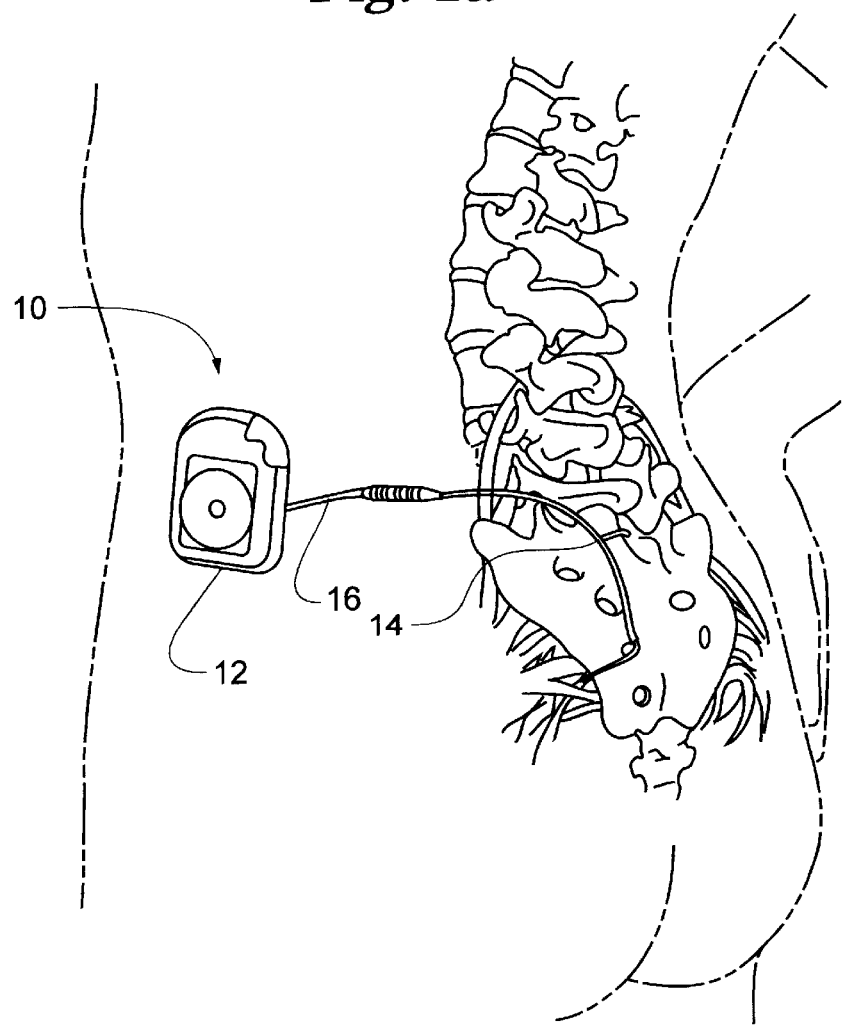
FIG. 1 shows an environment of an implantable medical device.
Figure 1B:
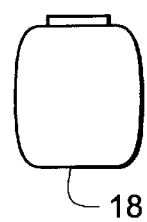
Figure 1C:
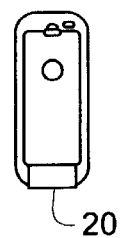
Figure 1D:
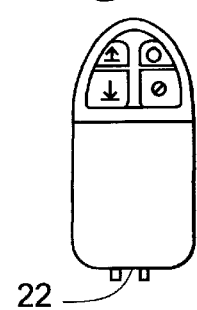

FIG. 1 shows the general environment of an implantable medical device 10 and more specifically an Implantable Neuro Stimulator (INS) 12 embodiment that includes a lead 14, a lead extension 16, an External Neuro Stimulator (ENS) 18, a physician programmer 20, and a patient programmer 22. Although an INS 12 embodiment is shown, the implantable medical device 10 could also be a pacemaker, a defibrillator, a drug delivery pump, a diagnostic recorder, a cochlear implant, and the like.

Figure 2:
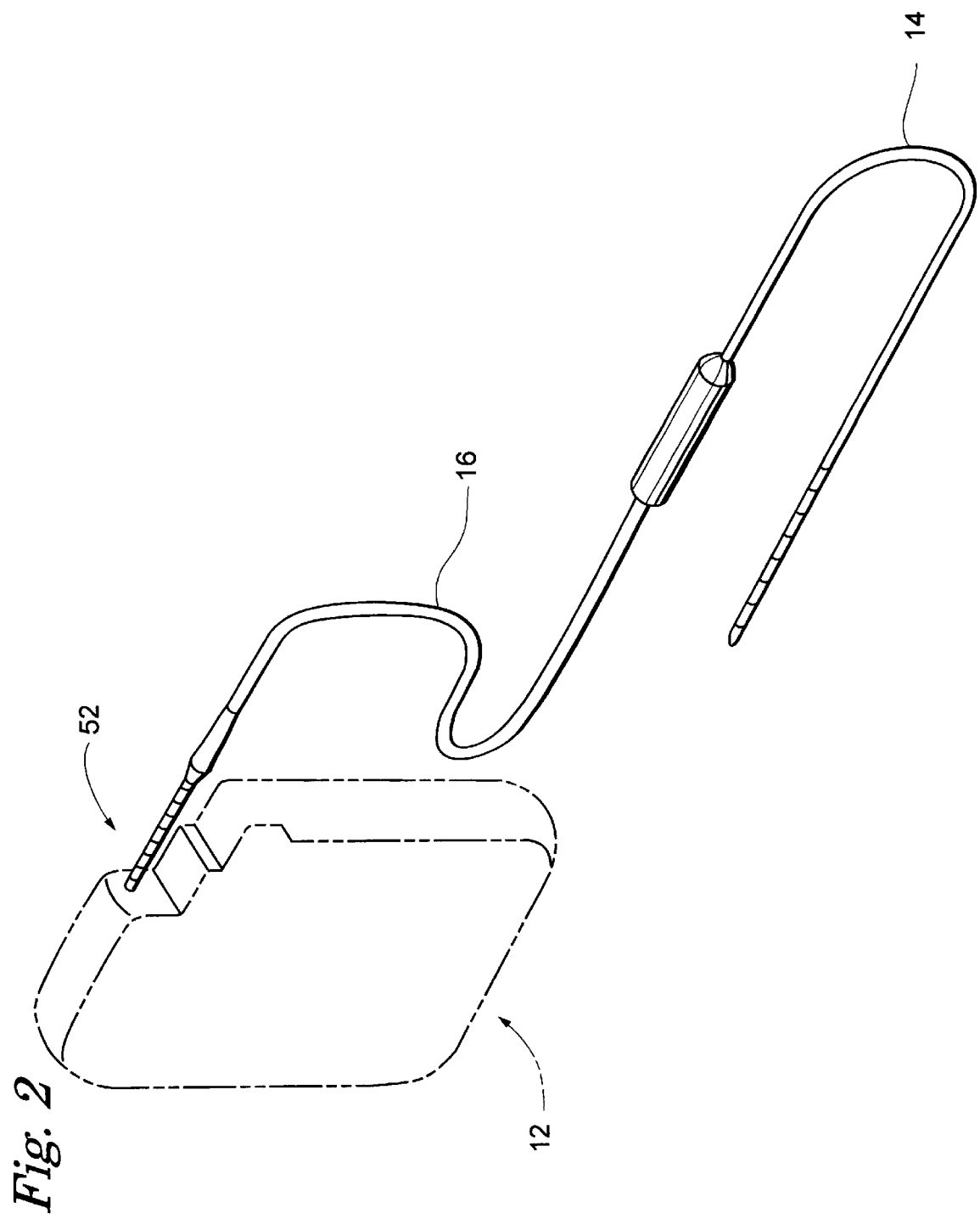
FIG. 2 shows a medical device embodiment.
Figure 3:
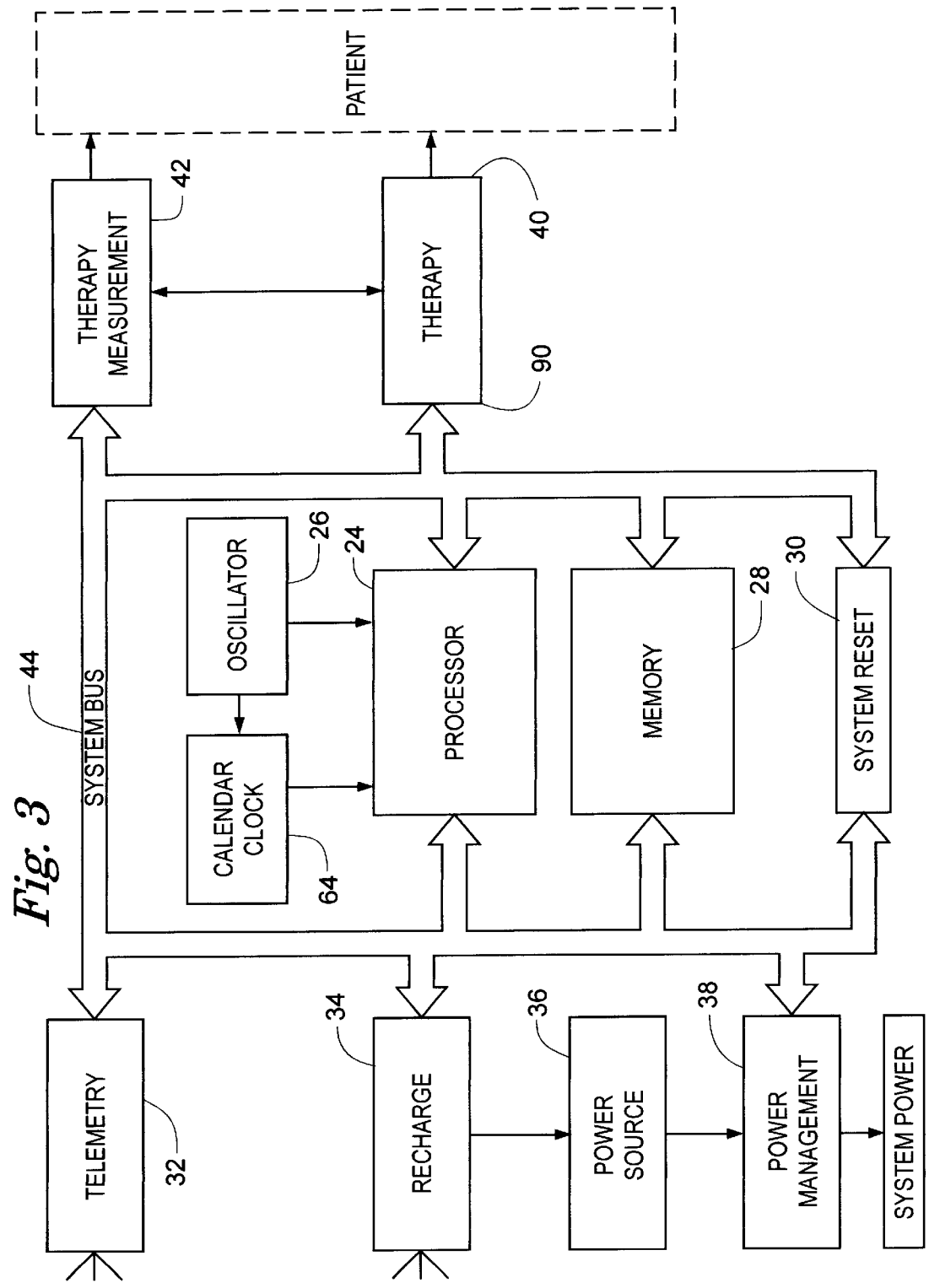
FIG. 3 shows a medical device block diagram embodiment.

FIG. 2 shows an Implantable Neuro Stimulator (INS) 12 medical device embodiment. FIG. 3 shows a block diagram of the INS 12 embodiment. The INS 12 generates a programmable electrical stimulation signal to influence a patient. The INS 12 comprises a processor 24 with an oscillator 26, memory 28, and system reset 30, a telemetry module 32, a recharge module 34, a power source 36, a power management module 38, a therapy module 40, and a therapy measurement module 42. Other versions of the INS 12 can include additional modules such as a diagnostics module. All components can be configured on one or more Application Specific Integrated Circuits (ASICs) except the power source 36. Also, all components are connected to bi-directional data bus 44 that is non-multiplexed with separate address 46 and data lines 48 (FIG. 6) except the oscillator 26, the calendar clock 64, and the power source 36. The system reset 30 controls operation of ASICs and modules during power-up of the INS 12, so ASICs and modules registers can be loaded and brought on-line in a stable condition. The INS 12 can be configured in a variety of versions by removing modules not necessary for the particular configuration and by adding additional components or modules. Primary cell, non-rechargeable, versions of the INS 12 will not include some or all of the components in the recharge module 34. All component of the INS 12 are contained within or carried on a housing 50 that is hermetically sealed and manufactured from a biocompatible material such as titanium. Feedthroughs 52 provide electrical connectivity through the housing 50 while maintaining a hermetic seal, and the feedthroughs 52 can be filtered to reduce incoming noise from sources such as cell phones. The INS 12 operates according to hardware and software parameters.

Figure 4:
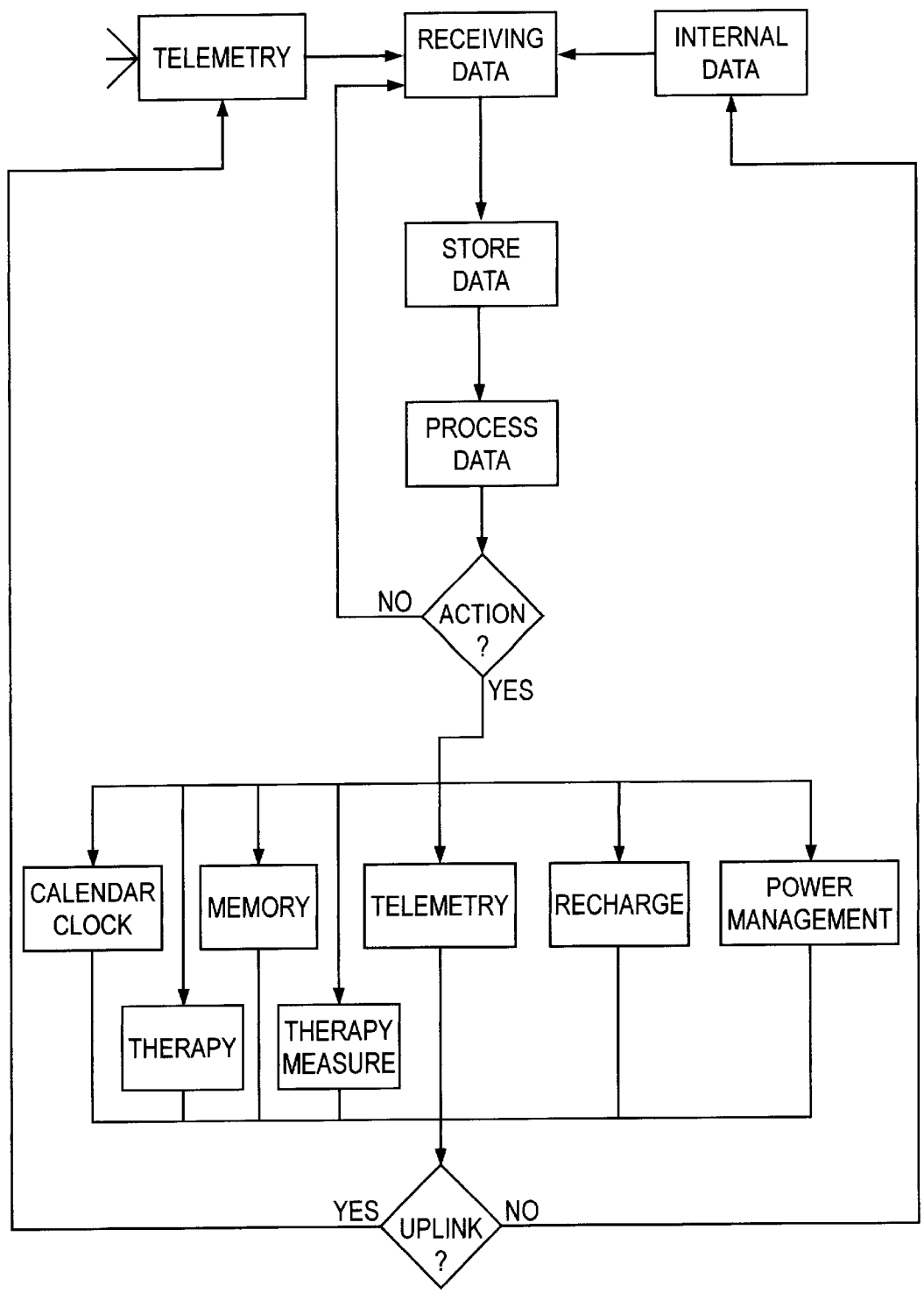
FIG. 4 shows a medical device basic operation flowchart embodiment.

FIG. 4 shows a basic INS 12 operation flowchart. Operation begins with when the processor 24 receives data from either telemetry or from an internal source in the INS 12. The received data is then stored in a memory 28 location. The data is processed by the processor 24 to identify the type of data and can include further processing such as validating the integrity of the data. After the data is processed, a decision is made whether to take an action. If no action is required, the INS stands by to receive data. If an action is required, the action will involve one or more of the following modules or components: calendar clock 64, memory 28, telemetry 32, recharge 34, power management 38, therapy 40, and therapy measurement 42. An example of an action would be to modify a programmed therapy. After the action is taken, a decision is made whether to prepare the action to be communicated, known as uplinked, to a patient programmer 22 or physician programmer 20 through the telemetry module 32. If the action is uplinked, the action is recorded in the patient programmer 22 or physician programmer 20. If the action is not uplinked, the action is recorded internally within the INS 12. An INS 12 as well as other implantable medical devices 10 can be configured for diagnostic emulation.

Figure 5:
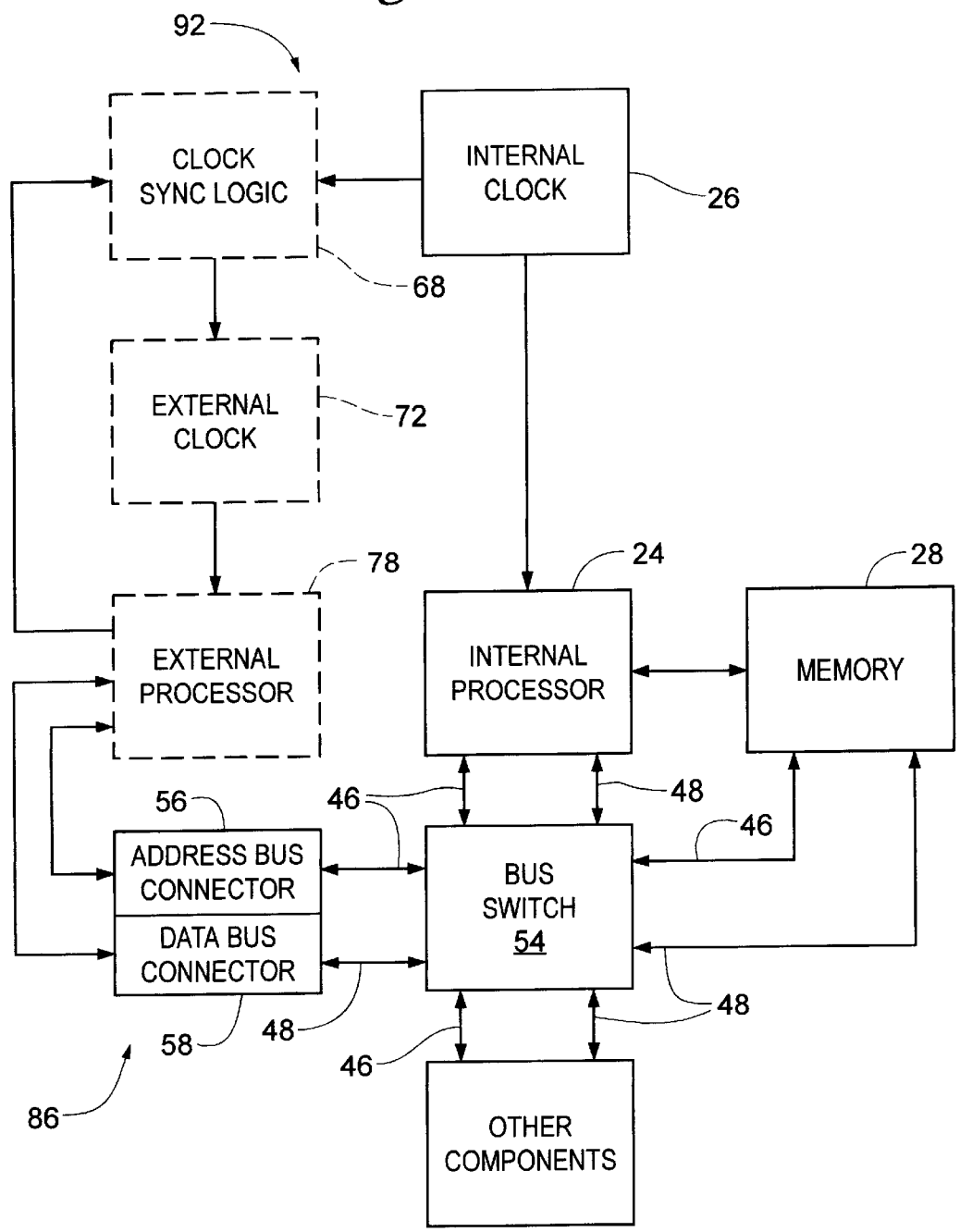
FIG. 5 shows a medical device diagnostic emulation block diagram embodiment.
Figure 6:
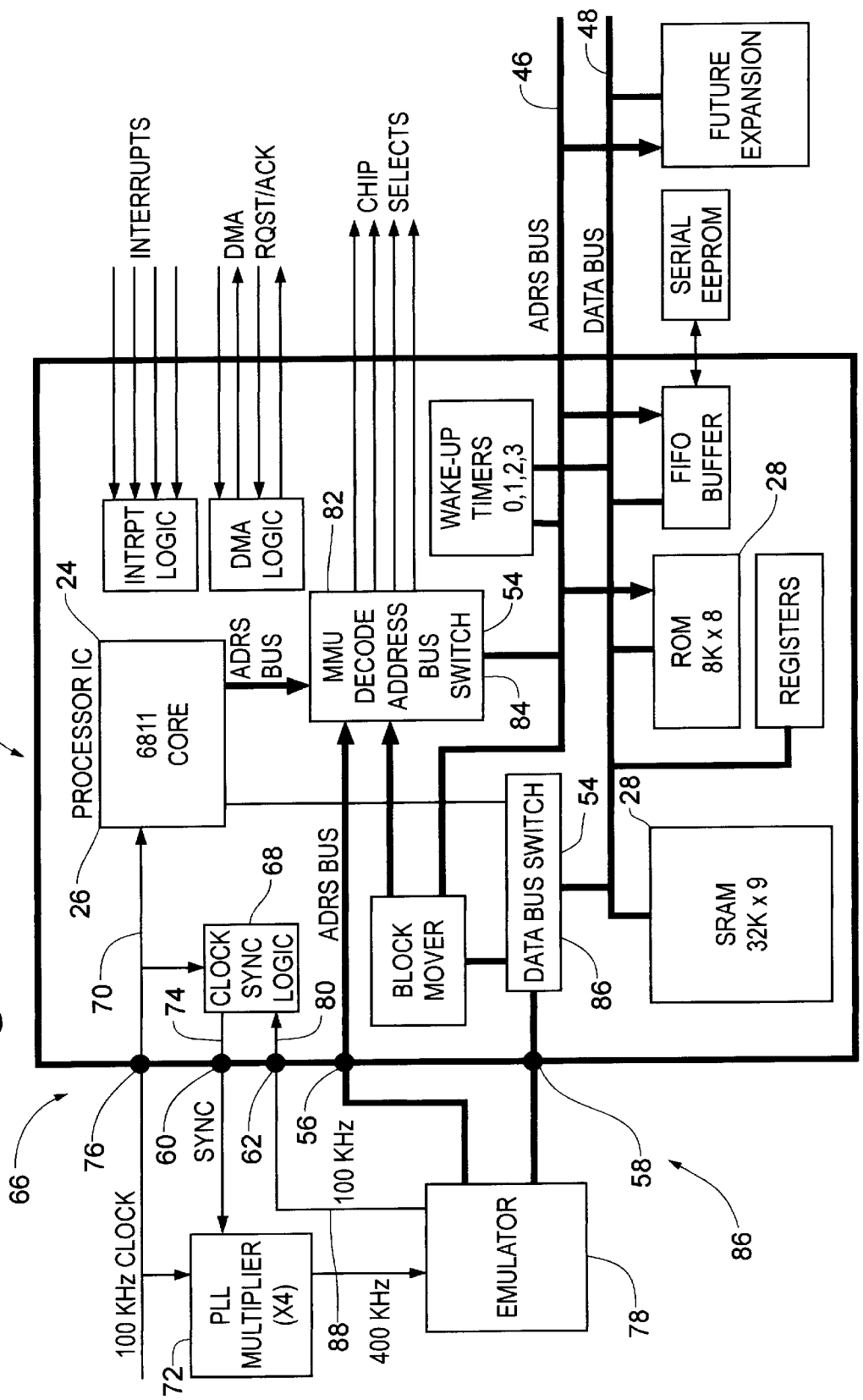
FIG. 6 shows a medical device detailed diagnostic emulation block diagram embodiment.

FIGS. 5 and 6 show block diagrams of an implantable medical device 10 configured for diagnostic emulation embodiment. The implantable medical device 10 configured for diagnostic emulation comprises an internal processor 24, an internal clock 26, memory 28, an address bus 46, a data bus 48, and a bus switch 54. The implantable medical device 10 can also include other components such as found in pacemakers, defibrillators, drug delivery pumps, diagnostic recorders, cochlear implants, the neuro stimulator embodiment described above, and the like. The components are carried in a housing 50 that is hermetically sealed and manufactured from a biocompatible material such as titanium, epoxy, ceramic, and the like. Feedthroughs 52 provide electrical connectivity through the housing 50 while maintaining a hermetic seal. If diagnostic emulation is desired while the medical device 10 is hermetically sealed, separate feedthroughs 52 can be provided or multipurpose feedthroughs 52 can be switched to allow a serialized data stream to recreate an address bus external connection 56, a data bus external connection 58, a clock sync connector 60, and a clock input connector 62. The implantable medical device 10 configured for diagnostic emulation can be a production medical device 10, so the diagnostic emulation results correspond more closely with actual production medical devices 10 than with partially disassembled products or laboratory simulations of products. The internal processor 24 has connectivity to many components of the implantable medical device 10 configured for emulation.

The internal processor 24 can be a micro processor ($\mu$P), ASIC state machine, or logic gate array. More specifically the processor 24 can be synchronous and operate on low power such as a Motorola 68HC11 synthesized core operating with a compatible instruction set. The internal clock 26 can operate at a frequency selected for the particular medical device 10 operation such as 100 KHz and greater speeds. The internal clock 26, also known as an oscillator, operates at a frequency compatible with the processor 24, associated components, and energy constraints such as 100 KHz or faster. The calendar clock 64 counts the number of seconds since a fixed date for date/time stamping of events and for therapy control such as circadian rhythm linked therapies. A clock sync circuit 66 includes clock sync logic 68 connected to the internal clock 26 with a clock line 70. The clock sync logic 68 is coupleable to the external clock 72 with a clock sync line 74 that has a clock sync connector 60. The clock line 70 has a clock connector 76 for connecting to the external clock 72. The clock sync logic 68 is coupleable to the external processor 78 with a clock input line 80 that has a clock input connector 62. The clock sync logic 68 synchronizes implantable medical device 10 internal logic with an external clock 72 typically operating at a different speed than the internal clock 26. For example the internal clock 26 can be synchronized with the external clock 72 by causing a rising edge of the internal clock 26 to occur at the same time as a rising edge of the external clock 72. The internal processor 24 is coupled to memory 28.

The memory 28 includes memory sufficient for medical device 10 operation such as volatile Random Access Memory (RAM) for example Static RAM, nonvolatile Read Only Memory (ROM), Electrically Erasable Programmable Read Only Memory (EEPROM) for example Flash EEPROM, and register arrays configured typically on ASICs. Direct Memory Access (DMA) is available to selected modules such as the telemetry module 32, so the telemetry module 32 can request control of the data bus 48 and write data directly to memory 28 bypassing the processor 24. The Memory Management Unit (MMU) 82 allows a larger amount of memory 28 to be addressed such a 1.0 Mb for future programming. Memory 28 is accessed through the address bus 46 and data bus 48.

The address bus 46 is coupled to the internal processor 24, memory 28, bus switch 54, and an address bus external connector 56. The address bus 46 and the data bus 48 are shows as separate lines, but a single line can be used for both the address bus 46 and the data bus 48 if the single line is multiplexed. The address bus 46 and the data bus 48 are bi-directional which permits the external processor 72 to access internal memory 28. All medical device modules 90 are typically connected to both the address bus 46 and the data bus 48. The address bus 46 operates with a word length compatible with the internal processor 24 such as twenty bit words. The data bus 48 is also coupled to the internal processor 24, memory 28, bus switch 54, and a data bus external connection 58. The data bus 48 operates with a word length compatible with the internal processor 24 such as eight bit words. An example of a bus timing embodiment is shown in Motorola's MC68HC11F1/D Technical Data Rev 3, pp. A-11 and A-12. The address bus 46 and data bus 48 are switched between the internal processor 24 and the external processor 78 with the bus switch 54, so one processor is active and the other processor is inactive.

The bus switch 54 is coupled to the address bus 46, the data bus 48, and the internal processor 24. The bus switch 54 serves as a means for bus switching to selectively switch the address bus 46 and data bus 48 from operation by the internal processor 24 to configuration for operation by an external processor 78 through the external address bus connection 56 and the external data bus connection 58. The bus switch 54 includes an address bus switch 84 and a data bus switch 86. The address bus switch 84 can be configured in the Memory Management Unit (MMU) 82. The data bus switch 86 can be configured as a group of tri-state logic gates that normally provide control of the data bus 48 to the internal processor 24 and when activated transfer control of the data bus 48 to the external processor 78. The bus switch 54 when activated decouples the internal processor 24 from the address bus 46 and the data bus 48 and couples an external processor 78 to the address bus 46 and data bus 48. The bus switch 54 has connectors 86 for coupling to the external processor 78.

The bus switch 54 has a bus switch external connector 86 that when activated is configured to couple an external processor 78 to the address bus 46 and the data bus 48 and decouple the internal processor 24 from the address bus 46 and data bus 48. The bus switch 54 includes an address bus switch 84 coupled to the address bus external connector 56 and the internal processor 24 and a data bus switch 86 coupled to the data bus external connector 58 and the internal processor 24. The external processor 78 is coupled through the address bus external connection 56 to the address bus 46 and the data bus external connector 58 to the data bus 48. Normally the bus switch 54 couples the internal processor 24 to the address bus 46 and the data bus 48, and the internal processor 24 has control over both the address bus 46 and the data bus 48. When activated by a logic signal the bus switch 54 decouples the internal processor 24, now the inactive processor, from the address bus 46 and the data bus 48. The internal processor 24 is decoupled by the address bus switch 84 switching an internal processor 24 address output to substantially zero, and the data bus switch 86 switching an internal processor 24 data bus output to high impedance. Additionally the bus switch 54 when activated holds the internal processor 24 in a reset condition. When the bus switch 54 is activated, the external processor 78, now the active processor, assumes control over the address bus 46 and the data bus 48. The active processor operates and has access to other modules 90 on the address bus 46 and data bus 48. The address bus external connector 56 and the data bus external connector 58 are coupleable to the external processor 78.

The external processor 78, also know as an emulator, can be a micro processor (μP) such as a Motorola 68HC11 operating at a higher speed than the internal processor, an ASIC state machine, a logic gate array, a personal computer or a more powerful computer. The external processor 78 has the capability to execute software and operate the address bus 46 and data bus 48 in a manner compatible with the internal processor 24. The external processor 78 includes memory for executing software and memory for recording software execution history. The software executed by the external processor 78 can be testing software to record operation of the implantable medical device 10 during testing and operating software to operate the implantable medical device 10 according to a test program. The testing software will typically have the capability to set a break point to stop execution of the operating software at a certain address. The testing software can reach results such as detection of nonconformance in medical device 10 hardware, firmware, and software. The external processor 78 can have an external clock 72 to enable the external processor 78 to operate at higher speeds than the internal processor 24 to reduce diagnostic testing time.

The external clock 72 can be a separate clock that is synchronized with the internal clock 26 or a Phase Lock Loop (PLL) multiplier connected between the clock connection 76 and the external processor 78. For example if the internal clock 26 is operating at 100 KHz and the PLL is a four times multiplier, then the external processor 78 will have a clock speed of 400 KHz. A clock divider will typically be placed between the external processor 78 and the clock sync logic 68 to provide an external processor clock input 88 to the clock sync logic 68. The clock divider can be integral to the external processor 78. The clock divider converts the external clock 72 to the frequency of the internal clock 26 for an input to the clock sync logic 68 to drive implantable medical device 10 components other than the internal processor 24 at the speed the components are designed to operate. Examples of clock connection embodiments are shown in Motorola's MC68HC11F1/D Technical Data Rev 3, pp. 2–4 and 2–5. Implantable medical devices typically use functional modules to perform functions.

A functional module 90 is connected to the address bus 46 and the data bus 48. The functional module 90 is a module from an implantable medical device 10 such as found in neuro stimulators, pacemakers, defibrillators, drug delivery pumps, diagnostic recorders, cochlear implants, and the like. For an implantable neuro stimulator 12 embodiment, the functional module 90 can be a therapy module 40, therapy measurement module 42, power management module 38, recharge module 34, telemetry module 32, and the like. Operationally coupling an implantable medical device 10 configured for emulation to an external processor 78 forms an emulation system.

An emulation system 92 comprises an internal processor 24, an internal clock 26, memory 28, an address bus 46, a data bus 48, an external processor 78, an external clock 72, and a bus switch 54. The internal clock 26 and memory 28 are both coupled to the internal processor 24. The address bus 46 is coupled to the internal processor 24 and memory 28. The data bus 48 is also coupled to the internal processor 24 and memory 28. The external processor 78 is coupled to the address bus 46 and the data bus 48. The external clock 72 is coupled to the external processor 78. A clock sync circuit 66 is connected between the external clock 72 and the internal clock 26 to synchronize internal logic with the external clock 72. A bus switch 54 is coupled to the address bus 46, the data bus 48, and a bus switch connector 86. The bus switch 54 when activated decouples the internal processor 24 from the address bus 46 and the data bus 48 and couples the external processor 78 to the address bus 46 and the data bus 48. The emulation system 92 can operate according to the following method.

Figure 7:
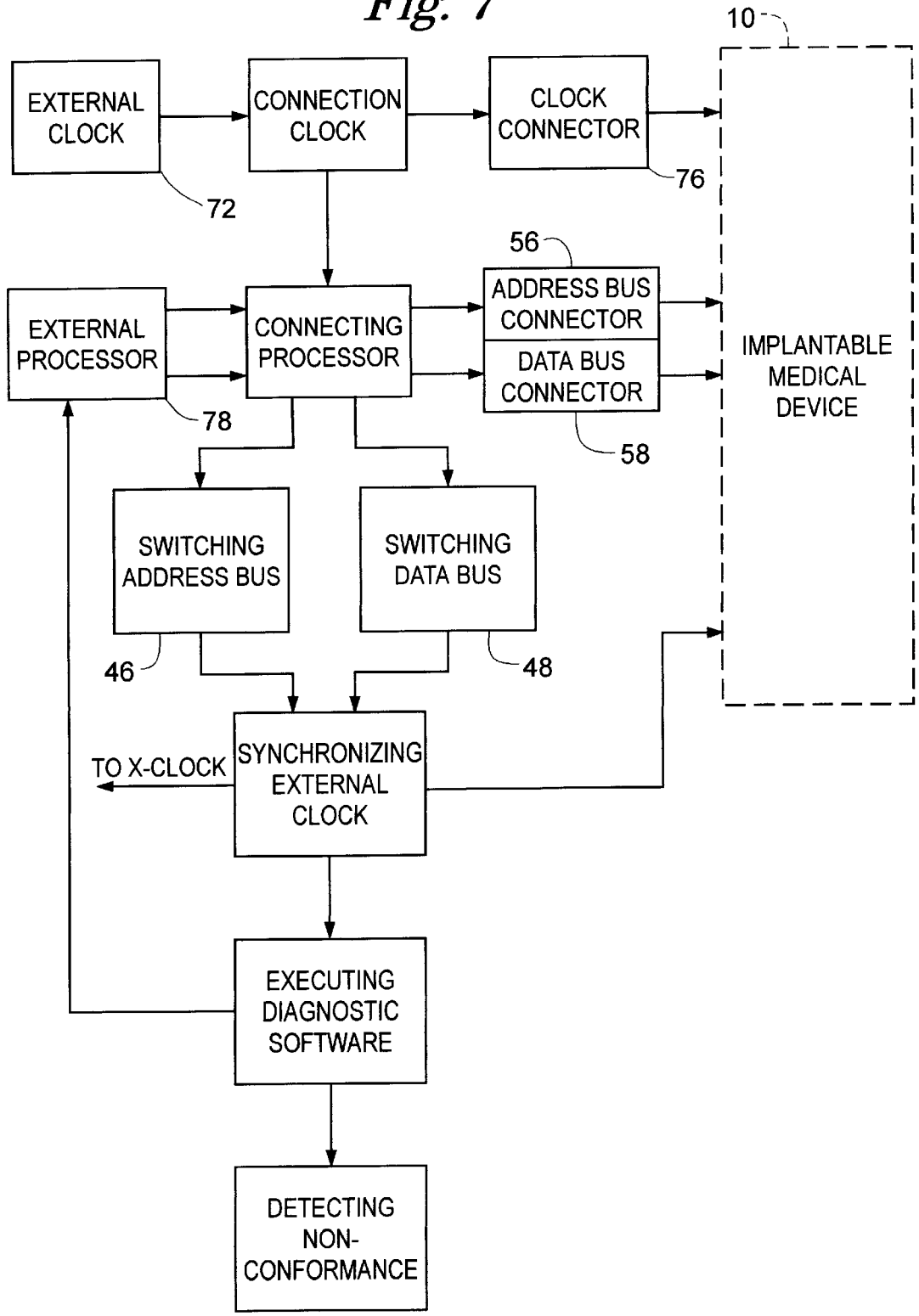
FIG. 7 shows a medical device method of diagnostic emulation embodiment.

FIG. 7 shows a method for implantable medical device 10 diagnostic emulation embodiment, and FIG. 6 shows a block diagram of an implantable medical device 10 configured for emulation embodiment. The method includes the following steps that are not necessarily listed in order. An external clock 72 is connected to a clock external connector 76. An external processor 78 is connected to an address bus external connection 56 and a data bus external connection 58. The address bus 46 is switched from the internal processor 24 to the external processor 78. Switching the address bus 46 can be accomplished by holding the inactive processor address at zero. The Memory Management Unit (MMU) 82 can serve as the address bus switch 84 by forcing the inactive processor address bus 46 to zero. Since the MMU 82 uses the sum of the two addresses from the external processor 78 and internal processor 24 to perform its calculations, the inactive processor is excluded from addresses. The data bus switch 86 switches the data bus 48 from the active processor to the inactive processor. Although the data bus 48 for the internal processor 24 and external processor 78 are connected together, the data bus switch 86 holds the inactive processor data bus connection in a high impedance state so that the inactive processor does not affect the active processor data bus 48. Some embodiments can also include additional elements such as medical device processor software executed with the external processor 78. The external processor 78 can also execute additional software to detect nonconformance in the medical device 10. Additional embodiments are also possible. Synchronization of the internal clock 26 and the external clock 72 can be better understood by examining their timing.

FIG. 8 shows a clock synchronization timing diagram embodiment with the internal clock pulse 94, external clock pulse 96, and external processor clock pulse 98. In some embodiments, the method can also include synchronizing the external clock 72 to the internal medical device logic. Synchronization occurs by lining up the leading edge of the internal clock pulse 94 with the external clock pulse 96 and the external processor clock pulse 98. The synchronization pulse 100 is generated by the clock sync logic 68.

Thus, embodiments of an implantable medical device configured for diagnostic emulation are disclosed that enhance diagnostic testing with capabilities such as faster testing, and more realistic testing. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. An implantable medical device configured for diagnostic emulation including being configured for coupling to an external processor, the implantable medical device comprising:
    an internal processor;
    an internal clock coupled to the internal processor;
    memory coupled to the internal processor;
    an address bus having an address bus external connection, the address bus being coupled to the internal processor and memory;
    a data bus having a data bus external connection, the data bus being coupled to the internal processor and memory;
    a bus switch coupled to the address bus, the data bus, and the internal processor, the bus switch having a bus switch external connector, wherein the bus switch external connector is adapted to receive an activation signal, wherein upon receiving the activation signal the bus switch is configured to couple the external processor through the address bus external connection to the address bus, couple the external processor through the data bus external connector to the data bus, and decouple the internal processor from the address bus and data bus, and
    a hermetically sealed housing, wherein the internal processor, internal clock, memory, and bus switch are all located within the housing.

2. The implantable medical device as in claim 1 further comprising the external processor, wherein the external processor is capable of executing computer code faster than the internal processor to reduce testing time.

3. The implantable medical device as in claim 1 wherein the implantable medical device is substantially a production implantable medical device.

4. The implantable medical device as in claim 1 wherein the bus switch when activated decouples the internal processor from the address bus and the data bus by switching an internal processor address output to substantially zero and switching an internal processor data bus output to high impedance.

5. The implantable medical device as in claim 1 wherein the internal processor has a reset condition, wherein the bus switch when activated holds the internal processor in the reset condition.

6. The implantable medical device as in claim 1 wherein the bus switch comprises an address bus switch and a data bus switch, wherein the address bus switch is coupled to the address bus and the data bus switch is coupled to the data bus.

7. The implantable medical device as in claim 6, further comprising a memory management unit wherein the address bus switch is part of the memory management unit.

8. The implantable medical device as in claim 6 wherein the data bus switch comprises tri-state logic gates.

9. The implantable medical device as in claim 1, further comprising the external processor and computer code executable on the external processor.

10. The implantable medical device as in claim 9 wherein the computer code detects nonconformance selected from the group consisting of nonconforming hardware, firmware, and software.

11. The implantable medical device as in claim 1, wherein the implantable medical device is adapted to be coupled to an external clock, the implantable medical device further comprising:
    clock sync logic;
    an external clock connector for coupling to the external clock; and
    a clock line coupling the clock sync logic to the internal clock and the external clock connector.

12. The implantable medical device as in claim 11 wherein the implantable medical device includes internal logic, wherein the external and internal clocks operate at different speeds, wherein the clock sync logic synchronizes the implantable medical device internal logic with the external clock.

13. The implantable medical device as in claim 1, further comprising a functional module connected to the address bus and the data bus.

14. The implantable medical device as in claim 13 wherein the functional module performs a function selected from the group of functions consisting of: therapy, therapy measurement, power management, recharge, and telemetry.

15. The implantable medical device as in claim 1 wherein the implantable medical device is selected from the group consisting of: a neuro stimulator, a pacemaker, a defibrillator, a drug delivery pump, a diagnostic recorder, and a cochlear implant.

16. An implantable medical device configured for diagnostic emulation including being configured for coupling to an external processor, the implantable medical device comprising:
    an internal processor;
    an internal clock coupled to the internal processor;
    memory used in normal non-emulation operation of the implantable device coupled to the internal processor;
    address bus having an external address bus connection, the address bus being coupled to the internal processor and memory;
    data bus having an external data bus connection, the data bus being coupled to the internal processor and memory;
    a means for bus switching to selectively switch the address bus and data bus from operation by the internal processor to configuration for operation by the external processor through the external address bus connection and the external data bus connection, and
    a hermetically sealed housing, wherein the internal processor, internal clock, memory, and means for bus switching are all located within the housing.

17. The implantable medical device as in claim 16 further comprising means for emulation, wherein the means for emulation comprises the external processor, wherein the external processor is capable of executing computer code faster than the internal processor to reduce testing time.

18. The implantable medical device as in claim 16 wherein the implantable medical device is substantially a production implantable medical device.

19. The implantable medical device as in claim 16, wherein the implantable medical device includes internal logic, wherein the internal clock and the external clock operate at different speeds, further comprising means for clock synchronization to synchronize the implantable medical device internal logic with the external clock.

20. An implantable medical device diagnostic emulation system, comprising:
   an internal processor;
   an internal clock coupled to the internal processor;
   memory coupled to the internal processor;
   an address bus coupled to the internal processor and memory;
   data bus coupled to the internal processor and memory;
   an external processor coupled to the address bus and the data bus;
   an external clock coupled to the external processor;
   internal logic;
   a clock sync circuit connected between the external clock to the internal clock to synchronize the internal logic with the external clock;
   a bus switch coupled to the address bus, the data bus and a bus switch connector, the bus switch when activated decouples the internal processor from the address bus and the data bus and couples the external processor to the address bus and data bus, and
   a hermetically sealed housing, wherein the internal processor, internal clock, memory, and bus switch are all located within the housing.

21. The implantable medical device as in claim 20 wherein the implantable medical device is substantially a production implantable medical device.

22. The implantable medical device as in claim 20, wherein the external processor is capable of executing computer code, wherein the external processor is capable of executing computer code faster than the internal processor to reduce testing time.

23. The implantable medical device as in claim 20 wherein the clock synchronization circuit comprises:
   clock sync logic;
   an external clock connector for coupling to the external clock; and
   a clock line coupling the clock sync logic to the internal clock and the external clock connector.

24. The implantable medical device as in claim 20, further comprising a memory device and recording software to record operation of the implantable medical device in the memory device during testing.

25. The implantable medical device as in claim 20, further comprising a memory device and testing software executable on the external processor to operate the implantable medical device by executing the testing software on the external processor and storing testing software results in the memory device.

26. The implantable medical device as in claim 20 wherein the implantable medical device is selected from the group consisting of: a neuro stimulator, a pacemaker, a defibrillator, a drug delivery pump, a diagnostic recorder, and a cochlear implant.

27. A method for implantable medical device diagnostic emulation, comprising:
   providing an implantable device including
      an internal processor, an internal clock coupled to the internal processor, memory coupled to the internal processor, an address bus coupled to the internal processor and coupled to the memory and having an address bus external connection, a data bus coupled to the internal processor and coupled to the memory and having a data bus external connection, a bus switch coupled to the address bus and to the data bus, and to the internal processor, a hermetically sealed housing, wherein the internal processor, internal clock, memory, and bus switch are all located within the housing, and internal medical device logic;
   providing an external processor;
   providing medical device processor software executable on the external processor;
   providing an external clock;
   connecting the external clock to-the clock external connector;
   connecting the external processor to the address bus external connection and the data bus external connection;
   switching the address bus from the internal processor to the external processor;
   switching the data bus from the internal processor to the external processor;
   synchronizing the external clock to the internal medical device logic;
   executing the medical device processor software with the external processor including the external processor reading from the implantable device memory and writing to the implantable device memory; and,
   detecting nonconformance in the medical device by the external processor.

28. The method as in claim 27 wherein the implantable medical device is substantially a production implantable medical device.

29. The method as in claim 27 wherein the executing the medical device software is executed faster in the external processor than in the internal processor.

30. The method as in claim 27 wherein the implantable medical device is selected from the group consisting of: a neuro stimulator, a pacemaker, a defibrillator, a drug delivery pump, a diagnostic recorder, and a cochlear implant.

* * * * *